US008024612B2

(12) United States Patent
Hilderscheid

(10) Patent No.: US 8,024,612 B2
(45) Date of Patent: Sep. 20, 2011

(54) REMOTE DIAGNOSIS SYSTEM FOR MEDICAL APPLIANCES OF MODULAR DESIGN

(75) Inventor: Thomas Hilderscheid, Altdorf (DE)

(73) Assignee: Siemens Aktiengesellschaft, Munich (DE)

( * ) Notice: Subject to any disclaimer, the term of this patent is extended or adjusted under 35 U.S.C. 154(b) by 909 days.

(21) Appl. No.: 11/882,804

(22) Filed: Aug. 6, 2007

(65) Prior Publication Data

US 2008/0034257 A1 Feb. 7, 2008

(30) Foreign Application Priority Data

Aug. 7, 2006 (DE) .......................... 10 2006 036 832

(51) Int. Cl.
*G06F 11/00* (2006.01)

(52) U.S. Cl. .............................. 714/30; 378/92; 378/207

(58) Field of Classification Search .................... 714/30; 378/114, 115, 116, 92, 207
See application file for complete search history.

(56) References Cited

U.S. PATENT DOCUMENTS

| 6,246,743 | B1 * | 6/2001 | Kopp et al. ..................... 378/19 |
| 6,275,559 | B1 * | 8/2001 | Ramani et al. .................... 378/4 |
| 6,325,540 | B1 * | 12/2001 | Lounsberry et al. ........... 378/207 |
| 6,505,966 | B1 * | 1/2003 | Guru ............................. 378/207 |
| 6,932,507 | B2 * | 8/2005 | Winkelmann ................. 378/207 |
| 7,120,547 | B2 * | 10/2006 | Herrmann et al. .............. 702/85 |
| 7,149,656 | B2 * | 12/2006 | Scher et al. .................... 702/183 |
| 7,181,648 | B2 * | 2/2007 | Bjorsne et al. .................. 714/26 |
| 7,240,251 | B2 * | 7/2007 | Popescu ....................... 714/704 |
| 7,795,590 | B2 * | 9/2010 | Takahashi et al. ....... 250/363.03 |
| 2003/0074489 | A1 | 4/2003 | Steger et al. |
| 2003/0101375 | A1 * | 5/2003 | Hohn ............................. 714/25 |
| 2006/0005081 | A1 * | 1/2006 | Seth et al. ...................... 714/39 |
| 2008/0123820 | A1 * | 5/2008 | Kendrick et al. ............. 378/207 |
| 2009/0224151 | A1 * | 9/2009 | Hatakeyama et al. ........ 250/307 |

* cited by examiner

*Primary Examiner* — Philip Guyton

(74) *Attorney, Agent, or Firm* — Harness, Dickey & Pierce, P.L.C.

(57) ABSTRACT

A method is disclosed for determining a configuration for a computer tomograph for the purpose of error diagnosis, a module, a computer tomograph and a system of appropriate design. The computer tomograph includes a multiplicity of detector modules. In at least one embodiment, a respective detector module is designed to have an identification device which is intended to provide a signature, the signature being uniquely associated with the respective module. The detector module transmits the measurement data it captures and its signature. The digital, electronic signature allows remote maintenance of the computer tomograph.

17 Claims, 1 Drawing Sheet

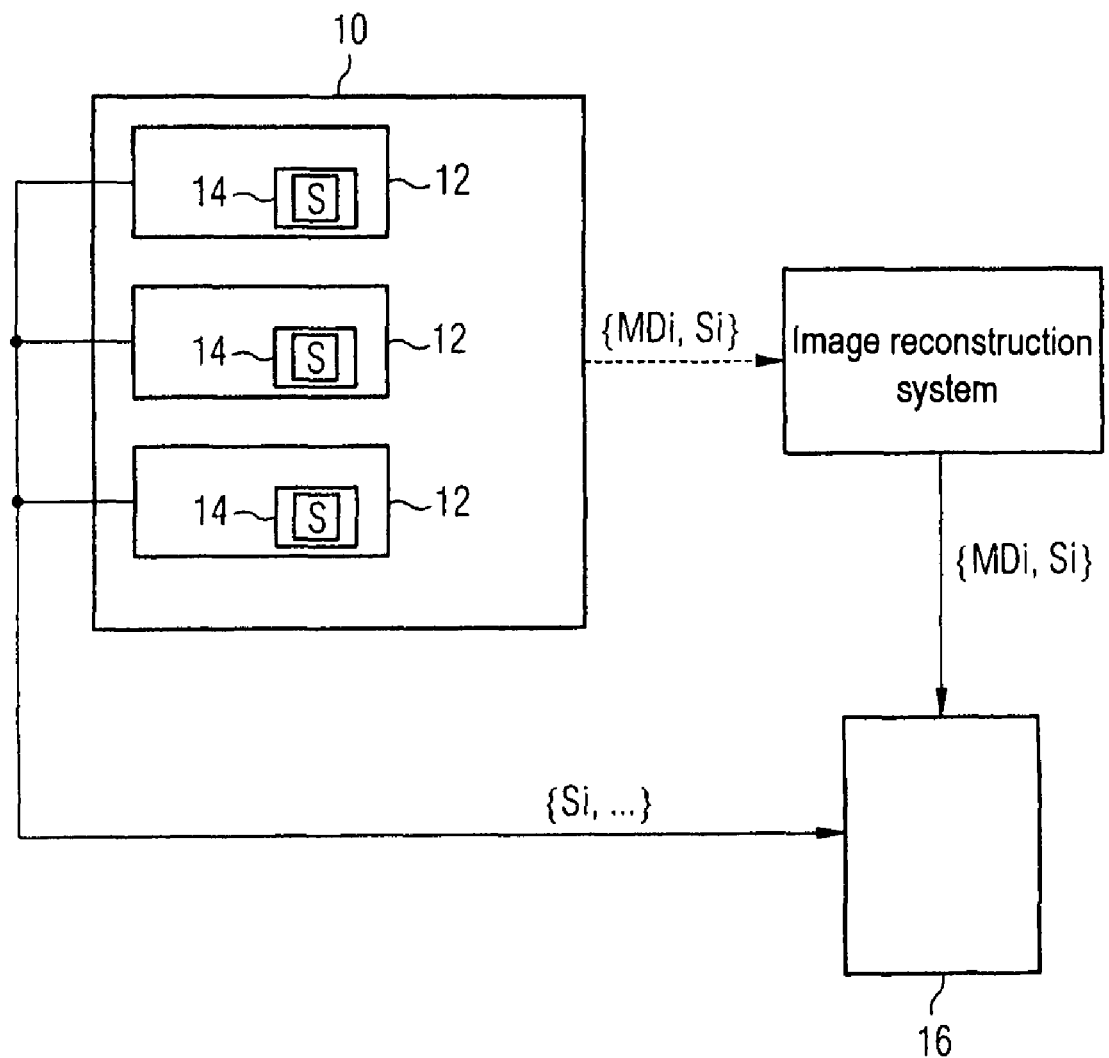

REMOTE DIAGNOSIS SYSTEM FOR MEDICAL APPLIANCES OF MODULAR DESIGN

PRIORITY STATEMENT

The present application hereby claims priority under 35 U.S.C. §119 on German patent application number DE 10 2006 036 832.0 filed Aug. 7, 2006, the entire contents of which is hereby incorporated herein by reference.

FIELD

Embodiments of the present invention are generally in the field of maintenance, diagnosis and monitoring of medical appliances of modular design, such as computer tomographs or X-ray appliances, which include a multiplicity of modules and components whose configuration and slots in the medical appliance can be of crucial importance for the diagnosis.

At least one embodiment of the invention may relate particularly to a method, a module, a medical appliance and/or a system for determining a configuration for a medical appliance for the purpose of error diagnosis, where the medical appliance comprises a multiplicity of modules for capturing measurement data.

BACKGROUND

A medical appliance, such as a computer tomograph, includes a multiplicity of detector modules which are respectively designed to capture measurement data. The detector modules are electronic components which are in different, similar or identical forms. In addition, there are also different types of detector modules.

During error diagnosis or functional monitoring of the computer tomograph, it is of crucial importance at what point within the medical appliance a respective detector module has been fitted. To diagnose the error (in an erroneous CT image or an erroneous image reconstruction), it is necessary to know what detector module at what slot within the medical appliance has been used to capture the data, in order to draw conclusions about a cause of error and in order to be able to restrict the error.

It is therefore found to be of crucial importance to know the association between a respective detector module and a slot within the medical appliance.

This has been solved in the prior art by a barcode system, including a bar code and a bar code reader. In this regard, each detector module has a unique identification, what is known as a serial number. The serial number is attached to the respective detector module as a sticker during production or following delivery of the respective module. The serial number can therefore be read manually by the maintenance personnel, and the bar code can furthermore also be read in by an optical scanner in situ.

The previous practice known from the prior art has a series of associated drawbacks.

One fundamental drawback can be seen in that fully automated remote diagnosis was not possible in the previous systems, since a service engineer in situ had first of all to read the respective serial number with the bar code. This practice is susceptible to error and cost intensive.

Another source of error in the case of the previous method from the prior art can be seen in that the respective configuration of the detector module or of the appliance may possibly not be recorded in the current version. Normally, a detector module is delivered by the factory in a particular configuration. When the detector module is fitted into the appliance or at a later time during the operation of the appliance, configuration changes on the detector module or other changes to the module (such as module replacement) are frequently made by the service engineer in situ.

Although provision is made for the service engineer to perform an update in a central database for every change, so that all changes ought to be available in theory—this practice is found not to be able to be implemented reliably in practice, since a service engineer generally does not update all changes in the database immediately. Remote diagnosis, where the data are read from a central database for the respective appliance and are analyzed, has therefore often been found not to be able to be implemented to date, since the database does not store the actual current state (for example even after a module has been replaced by another module in the panel, where the module replacement has not been updated in the database by the service engineer). Reliable access to the respective current configuration of the medical appliance is therefore not possible in the prior art, which means that remote diagnosis must often fail.

Appliances which include a multiplicity of modules and which perform automatic interface adaptation are known from US patent application US 2003/0074489 A1 ("Steger"), for example. However, this document provides no kind of indication about reliable error diagnosis and about determining the configuration of an appliance for use in the medical field. Steger describes a method in which the modules are recorded and in which their interface requirements are determined.

SUMMARY

In consideration of the aforementioned and other drawbacks of the known methods from the prior art, in at least one embodiment of the present invention, a way of making reliable remote diagnosis of a medical appliance of modular design is made possible as is a way of automating, and hence simplifying, and improving the determination of a configuration of the medical appliance.

In at least one embodiment of the present invention, a method is disclosed for determining a configuration for a medical appliance, by an appropriate module which is intended to be fitted into the medical appliance, by a medical appliance of appropriate design and/or by a system.

In at least one embodiment, a method is disclosed for determining a configuration for an appliance, particularly a medical appliance, for the purpose of error diagnosis and/or monitoring of operation of the appliance, where the medical appliance comprises a plurality of modules which are intended, in particular, to capture measurement data, the modules being fitted in the appliance or being intended to be fitted into the appliance, the method comprising:

a signature is provided in a respective module, the signature being uniquely associated with the respective module, if appropriate, the signature is transmitted and/or stored after the module has been fitted into the medical appliance, the respective current configuration of the medical appliance is determined by identifying a respective slot for all or selected modules in the appliance in question by automatically recording the signature for the respective module, in particular without the need for user inputs or other requirements to be met, and where the signature is automatically processed, transmitted and/or stored together with measurement data captured by the module.

In at least one example embodiment, the medical appliance is a computer tomograph which includes 40 to 50 detector modules as modules, where a respective detector module is intended to capture the CT data. However, alternative embodiments relate to other medical appliances which are likewise of modular design, such as NMR appliances, X-ray appliances, ultrasound appliances or the like. Accordingly, the modules may be not only detector modules but also other separate components which need to be incorporated into a medical appliance. Normally, the modules are used to capture measurement data which—in the case of a computer tomograph—are used for later image reconstruction.

The slot may be output of a position, an appliance-specific statement or another piece of information which relates the module to the appliance.

Within the context of embodiments of the invention, the term "configuration" is to be understood in the broad sense and covers all influencing variables in relation to the respective medical appliance. In particular, the configuration covers the determination of what modules are fitted at what slot within the appliance. In other words, the configuration covers an association between modules and slots. In the example embodiment, this association relation is unique. However, alternative embodiments provide for other association options here, particularly a 1:n association. Furthermore, the configuration may also cover further parameters, such as the type, embodiment and/or other settings in relation to the respective module. In addition, it is also possible to take account of parameters which relate to the respective medical appliance, such as the fundamental operating system, IT background data, for example computer power, storage capacity, transmission capacity etc.

In a more complex development of at least one embodiment of the invention, provision is made for further physical parameters to be taken into account here, such as a temperature measured on the respective detector.

In the example embodiment, the signature is an electronic signature which is intended to identify the respective module. The electronic signature is preferably in a 1:1 association with the respective module. In the example embodiment, the signature is provided by an identification device which is associated with the module as an additional separate component.

Preferably, the signature is provided when the detector module is delivered. Alternative embodiments provide for the signature not to be provided until a later time. However, it must be in place and stored no later than when the module is fitted into the medical appliance. The identification device for providing the signature has an interface to the detector module. This makes it possible for the electronic signature to be processed further and transmitted together with the data which are to be processed by the module. Normally, the signature is forwarded to another entity for processing together with the measurement data from the detector module. However, it is alternatively also possible for other interfaces to be provided here in order to be able to read the signature from another, external appliance and to forward it to another entity for processing via a separate interface.

As already mentioned, the example embodiment of the present invention relates to error diagnosis and monitoring of CT appliances with detector modules. However, alternative embodiments provide other medical appliances of modular design here. It is similarly possible for the inventive method to be applied not exclusively for the purpose of error diagnosis, but rather for monitoring the currently progressing operation of the medical appliance and determining current configurations for the appliance or the modules, for example.

Advantageously, the configuration of the medical appliance can be determined in fully automated fashion. Normally, it is done during normal operation of the appliance or the detector and requires no separate or additional user actions or inputs. In addition, remote determination is possible. In other words, a central entity can determine what module is at what slot within the medical appliance in the panel if the central entity is able to interchange data with the respective appliance. This may involve permanent data interchange (that is to say a continually present data link) or temporary data interchange. The determination of the configuration and/or the recording of the signature can therefore advantageously be carried out via an interface by a remote entity—and hence "remotely". Manual control steps by a service engineer can therefore advantageously be dispensed with, which significantly increases the reliability of the system overall.

In one example embodiment of the invention, provision is made for the signature to be processed and/or stored together with the measurement data captured by the module. This has the advantage that an additional interface does not need to be provided for transmitting the signature. Usually, the signature is stored in a specific data structure which is coupled or appended to the respective measurement data from the module. The signature can then be processed further together with the measurement data. Normally, the measurement data are forwarded together with the signature to an image reconstruction system which uses the captured measurement data to construct an image. In the event of an error, the signature associated with the measurement data can now be used to gather further information about the capture of the measurement data. The signature can advantageously be used to infer what detector modules have been used to capture the data.

Preferably, at least one embodiment of the inventive method comprises two phases:
1) A production phase in which a module test is also performed and in which the signature is provided and associated with a module;
2) An operating phase in which the respective module has already been fitted into the medical appliance and in which the medical appliance is in operation or in use. In this operating phase, the current configuration of the appliance can be determined. In particular, error diagnosis is performed during the operating phase. Usually, the signature is also processed, transmitted and/or stored during the operating phase. In one alternative embodiment, however, it is also possible for the signature to be processed, transmitted and/or stored not during the operation of the medical appliance but rather, by way of example, during a down time for the medical appliance, so as not to disrupt the use of the appliance. In this embodiment, a special analysis phase is therefore provided in which signature-specific data are read and are used for analysis. In this context, it is possible to access already stored data records (that is to say stored measurement data with already stored signatures) or to generate the respective values just for the purpose of analysis—and hence virtually.

In one advantageous complex example embodiment of the invention, provision is made for the signature to be processed, transmitted and/or stored, in principle, whenever measurement data are captured and processed or transmitted by the module. In this embodiment, provision is thus made for the measurement data transmitted from the module to the image reconstruction system to comprise, in principle, a signature for the module capturing the respective measurement data.

This has the advantage that, in principle, it is always reliably possible to resort to a respective signature for any image reconstruction for the purpose of further analysis of the measurement data.

Alternatively, however, provision may be made for the signature not to be transmitted afresh each time, but rather only on the basis of configurable criteria. The criteria may be specific to timing and/or situation. By way of example, it may be set that the signature is transmitted only after a particular time interval, that it is transmitted only per image which is to be generated or per patient or on the basis of other dynamically adaptable criteria. This allows storage space and transmission capacity to be saved.

In a still further restricted example embodiment, provision is made for the signature to be transmitted and/or stored only once in each case. In this embodiment, provision is made for the signature to be transmitted and/or stored when the respective module is started up for the first time. So long as the respective module remains in operation unchanged, the signature is not repeatedly transmitted and/or stored again. As soon as there is a change on the module, however, the signature is respectively retransmitted and/or stored again, so that there is the certainty that the current signature is always stored in the system.

To avoid data redundancies in relation to the signature, provision is advantageously made for the signature to be processed, transmitted and/or stored when the respective module is started up in the medical appliance and/or when there is a change for the module. Hence, when the module has been started up for the first time, the signature is then stored again if there is a change on the module, for example as a result of replacement or as a result of removal of the respective module.

Advantageously, at least one example embodiment of the inventive method can always be used to record the respective current configuration of the medical appliance in the panel remotely, even following module replacement. The captured measurement data can advantageously be rated and analyzed using a reliably updated configuration.

Another advantage can be seen in that it is possible to avoid the manual practice when delivering the respective modules. It is no longer necessary for all detector modules to be scanned in the correct order using a bar code scanner in order to be able to determine the slot for the respective detector module in the appliance reliably at a later time. This allows sources of error as a result of incorrect or missing associations to be advantageously avoided. In one example embodiment, provision is made for the inventive practice to be used in addition to the practice previously applied from the prior art; that is to say that the electronic signature is envisaged and provided in addition to the serial number which is stuck on (as the previous device of identification). This gives rise to the advantage that previous detector modules can be used unchanged.

For future developments, alternative embodiments have provision for the serial number no longer to need to be recorded imperatively in the system but rather to be able to be stored just optionally, however. The appliance configuration is then recorded with the respective modules exclusively on the basis of the electronic signature.

Normally, the signature is provided by an identification device which is arranged on or associated with the module as an additional separate component. An identification device generates a respective signature, in which case it is necessary to ensure that each identification device generates a different signature in order to allow later identification of the module on the basis of the signature. Each module is equipped with an appropriate identification device upon delivery. Normally, an electronic signature is used. If, in alternative embodiments, another form of signature is meant to be used, for example physical signatures, however, then it must be ensured that a sufficient level of resolution can be achieved, since the respective modules to be identified are relatively close to one another in the medical appliance.

In principle, the electronic identification device needs to be permanently and inseparably associated with the respective module. Similarly, the signature for a respective module is unalterable in order to be able to reliably preclude misassociations.

The inventive solution has been described above with reference to example embodiments of the method. Advantages, features and alternative embodiments mentioned in this context can likewise be transferred to the other solutions for the inventive problem. In other words, embodiments of the inventive system for determining a configuration, the module and/or the medical appliance can also be developed using the features which have been mentioned in connection with embodiments of the inventive method, and vice versa.

A system is also disclosed for determining a configuration for a medical appliance for the purpose of error diagnosis and/or monitoring, where the medical appliance comprises a plurality of modules for capturing measurement data which are fitted or integrated in the medical appliance, the system comprising:

an electronic device which is associated with a respective module and, in particular, is integrated in the module and is used to provide a signature identifying the module, and a central error diagnosis entity which is intended to automatically determine the respective current configuration of the appliance by identifying a slot for all or selected modules in the appliance in question by virtue of the central error diagnosis entity accessing the respective electronic identification device in order to record the respective signature for the module.

In one example embodiment of the inventive system, the system additionally includes a memory for storing the signature. In this case, the memory may be designed to be alternatively in the module, in a hierarchically superordinate apparatus, in the medical appliance and/or in an external entity (for example in an image reconstruction system).

In one example embodiment of the invention, the error diagnosis entity is a central entity. However, it may be possible to provide a plurality of error diagnosis entities. Usually, they are arranged remotely from the medical appliance, so that "remote" access is necessary. Accordingly, the error diagnosis entity needs to have a permanent or an intermittently existing data link to the respective appliance and/or to the modules in the appliance.

The system may include an image reconstruction system which is intended to reconstruct images on the basis of the measurement data determined by the appliance. In line with at least one embodiment of the invention, the appliance sends not only the measurement data to the image reconstruction system but also the respective signature which points to the detector module which has been used to capture the measurement data, so that at least in the event of an error it is possible to infer the detector module with the corresponding parameters.

Normally, the identification device is an additional component which is fitted permanently and unalterably in the detector module. Alternatively, an already existing component may be modified such that it provides a unique electronic signature identifying the respective module.

Another solution to the problem is a module which is intended to capture measurement data and to be fitted into a medical appliance, where the module includes an electronic identification device which is intended to provide a signature, the signature being uniquely associated with the respective module.

Another solution to the problem is a medical appliance which is designed to have means for error diagnosis and/or for monitoring and includes a module of the aforementioned type.

BRIEF DESCRIPTION OF THE DRAWINGS

The present invention is explained below with reference to an example embodiment which should be read in conjunction with FIG. 1 and which shows further advantages, features and alternative embodiments of the invention.

FIG. 1 shows a schematic, synoptic illustration of a medical appliance having a plurality of modules and a central error diagnosis entity in line with an example embodiment of the invention.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

As FIG. 1 shows, an example embodiment of the inventive system includes a computer tomograph 10 which comprises a plurality of detector modules 12. A detector module 12 includes an identification device 14 which is intended to provide an electronic signature S.

The signature S is a digital signature, that is to say a digital identification code which can be read by an ordinary computer and does not require a special reader.

The computer tomograph 10 and/or the detector modules 12 are able to interchange data with an error diagnosis entity 16 which is intended to monitor the operation of the computer tomograph 10 and which, in the event of an error, analyzes the error in the computer tomograph 10. Usually, the error diagnosis entity 16 is in the form of a central entity which performs remote diagnosis for the computer tomograph 10.

The detector module 12 is used to capture measurement data MD. In line with an example embodiment of the invention, the respective signature S is transmitted and/or stored in addition to the captured measurement data. Usually, a tuple $(S_i, MD_i)$ is thus stored, where the reference symbol $S_i$ refers to the signature which has been recorded by the i-th detector module $12_i$, and where the reference symbol $MD_i$ refers to the measurement data which have been captured by the i-th detector module.

In one variant of an example embodiment of the invention, provision is made for, in principle, the measurement data MD always to have the associated signature S transmitted to the image reconstruction system. In the event of an error or in the case of periodic monitoring of the computer tomograph 10, the central error diagnosis entity 16 analyzes the images from the computer tomograph 10 which have been reconstructed by the image reconstruction system. In this case, in line with an example embodiment of the invention, the signature S can be used to derive what detector module has been used to record the image.

Alternatively or cumulatively, it is possible to perform a module test in which each individual detector module 12 is checked for freedom from error sequentially or in parallel. For this, each detector module 12 can interchange data with the central error diagnosis entity 16. As indicated in FIG. 1, the respective detector module 12 transmits not only the signature $S_i$ but preferably also further parameters to the central error diagnosis entity 16. This is intended to be shown by the dots inside the curly brackets on the connecting line between the detector modules and the central error diagnosis entity. The further parameters are, in particular, the slot for the respective module. This means that the central error diagnosis entity 16 can uniquely and automatically infer what detector module 12 is fitted at what location in the computer tomograph 10. An association between the slot and the respective detector module 12 is therefore possible automatically and easily. This means that it is always possible to ascertain the current configuration of the computer tomograph 10 and, in the event of an error, it is possible to infer the faulty detector module 12 if appropriate.

If there has been change in the configuration of the computer tomograph 10 in the meantime (for example as a result of particular detector modules 12 being replaced), it is advantageously possible to ascertain the respective current configuration of the computer tomograph 10 with the currently positioned detector modules 12 remotely too. This is an advantage which proves to be very relevant in practice, since with 40 to 50 detector modules 12 fitted in a computer tomograph 10, searching for an error within the large number of detectors 12 is a time-consuming and cost-intensive process. In line with the invention, the error search can be improved significantly by restricting it to the faulty detector module.

In conclusion, it should be pointed out that the detailed description of the figures above is just one example embodiment which can be modified in different ways by a person skilled in the art without departing from the scope of the invention. In addition, other physical implementations of embodiments of the invention are also possible. In particular, it is obvious to a person skilled in the art that the embodiments of the invention can also be implemented as a heterogeneous system, partly or fully by software and/or hardware modules and/or in a form distributed over a plurality of physical products.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to Floppy Disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a configuration for a medical appliance for error diagnosis, the medical appliance including a plurality of modules for capturing measurement data intended to be fitted into the medical appliance, the method comprising:
   providing a signature for a respective module, the signature being uniquely associated with the respective module; and
   automatically determining a current configuration of the medical appliance after the modules are fitted into the medical appliance by identifying a slot for at least one of the plurality of modules in the medical appliance by automatically recording the respective signature of the at least one module, the signature being at least one of automatically processed, transmitted and stored together with measurement data captured by the at least one module; wherein the method is dividable into two phases including:
      a production phase, before the respective module is fitted into the medical appliance, in which the signature is provided, and
      an operating phase, after the respective module has been fitted into the medical appliance, in which error diagnosis is performable and in which at least one of the signature is at least one of processed, transmitted and stored and in which the current configuration of the appliance is determinable.

2. The method as claimed in claim 1, wherein the medical appliance is a computer tomograph.

3. The method as claimed in claim 1, wherein the signature is at least one of transmitted from the module to at least one of an image reconstruction system and an error diagnosis entity, and stored.

4. The method as claimed in claim 1, wherein the signature is retrievable by a remote entity via a provided interface.

5. The method as claimed in claim 1, wherein at least one of the configuration is determinable and the signature is recordable by a remote entity via at least one provided interface.

6. The method as claimed in claim 1, wherein the signature is at least one of transmitted and stored on the basis of configurable criteria.

7. The method as claimed in claim 1, wherein the signature is at least one of processed, transmitted and stored at least one of when the module is started up in the medical appliance and when the module is changed.

8. The method of claim 1, wherein the current configuration is indicative of an association between the plurality of detector modules and respective slots.

9. A hardware detector module, intended to capture measurement data and to be fitted into a medical appliance, the detector module comprising:
   an electronic identification device configured to provide a signature for the hardware detector module, the signature being uniquely associated with the hardware detector module and the hardware detector module being configured such that the signature is at least one of automatically processable, transmittable and storable together with the captured measurement data; wherein
      the signature for the hardware detector module is provided in a production phase, before the hardware detector module is fitted into the medical appliance, and
      a configuration of the medical appliance is automatically determined after the hardware detector module is fitted into the medical appliance by identifying a slot for the hardware detector module in the medical appliance by automatically recording the signature of the hardware detector module, wherein the configuration of the medical appliance is determined in an operating phase, after the hardware detector module has been fitted into the medical appliance, in which error diagnosis is performable and in which the signature is at least one of processed, transmitted and stored.

10. A medical appliance comprising:
  means for at least one of error diagnosis and monitoring; and
  a hardware detector module as claimed in claim 9.

11. A hardware system for determining a configuration for a medical appliance for the purpose of error diagnosis, the medical appliance including a plurality of detector modules for capturing measurement data which are at least one of fitted in the medical appliance and intended to be fitted into the medical appliance, the system comprising:
  at least one electronic identification device associated with a respective detector module and used to provide a signature identifying the detector module; and
  an error diagnosis entity configured to automatically determine a current configuration of the medical appliance by identifying a slot for at least one of the plurality of detector modules in the medical appliance in question by virtue of the error diagnosis entity reading the respective signature for the detector module from the electronic identification device together with the data captured by the detector module; wherein
    the current configuration is indicative of an association between the plurality of detector modules and respective slots, and
    the determining of the of the configuration of the medical appliance is dividable into two phases including,
      a production phase, before the respective detector module is fitted into the medical appliance, in which the signature is provided, and
      an operating phase, after the respective detector module has been fitted into the medical appliance, in which error diagnosis is performable and in which at least one of the signature is at least one of processed, transmitted and stored and in which the current configuration of the medical appliance is determinable.

12. A method for determining a configuration for a medical appliance for error diagnosis, the medical appliance including a plurality of detector modules for capturing measurement data intended to be fitted into the medical appliance, the method comprising:
  providing a signature for a respective detector module, the signature being uniquely associated with the respective detector module; and
  automatically determining a current configuration of the medical appliance after the detector modules are fitted into the medical appliance by identifying a slot for at least one of the plurality of detector modules in the medical appliance by automatically recording the respective signature of the at least one detector module, the signature being at least one of automatically processed, transmitted and stored together with measurement data captured by the at least one detector module; wherein
  the medical appliance is a computer tomograph, and
  the method is dividable into two phases including:
    a production phase, before the respective detector module is fitted into the medical appliance, in which the signature is provided, and
    an operating phase, after the respective detector module has been fitted into the medical appliance, in which error diagnosis is performable and in which at least one of the signature is at least one of processed, transmitted and stored and in which the current configuration of the appliance is determinable.

13. The method as claimed in claim 12, wherein the signature is at least one of transmitted from the detector module to at least one of an image reconstruction system and an error diagnosis entity, and stored.

14. The method as claimed in claim 12, wherein the signature is retrievable by a remote entity via a provided interface.

15. The method as claimed in claim 12, wherein at least one of the configuration is determinable and the signature is recordable by a remote entity via at least one provided interface.

16. The method as claimed in claim 12, wherein the signature is at least one of transmitted and stored on the basis of configurable criteria.

17. The method as claimed in claim 12, wherein the signature is at least one of processed, transmitted and stored at least one of when the detector module is started up in the medical appliance and when the detector module is changed.

* * * * *